United States Patent [19]

Leach

[11] 4,022,843

[45] * May 10, 1977

[54] LIQUID PHASE METHYLATION OF ORTHO CRESOL

[75] Inventor: Bruce E. Leach, Ponca City, Okla.

[73] Assignee: Continental Oil Company, Ponca City, Okla.

[*] Notice: The portion of the term of this patent subsequent to Sept. 7, 1993, has been disclaimed.

[22] Filed: Aug. 25, 1975

[21] Appl. No.: 607,733

[52] U.S. Cl. ............................................. 260/621 R
[51] Int. Cl.$^2$ ....................................... C07C 39/06
[58] Field of Search ........ 260/621 R, 624 R, 624 C

[56] References Cited

UNITED STATES PATENTS

| | | | |
|---|---|---|---|
| 3,422,156 | 1/1969 | Thoma | 260/621 R |
| 3,426,358 | 2/1969 | Schlichting | 260/621 R |
| 3,624,163 | 11/1971 | De Bel | 260/621 R |
| 3,707,569 | 12/1972 | van Sorge | 260/621 R |
| 3,737,466 | 6/1973 | Sharpe et al. | 260/621 R |

FOREIGN PATENTS OR APPLICATIONS 717,588   10/1954   United Kingdom ........... 260/621 R

*Primary Examiner*—James O. Thomas, Jr.
*Assistant Examiner*—W. B. Lone
*Attorney, Agent, or Firm*—Cortlan R. Schupbach, Jr.

[57] ABSTRACT

Ortho cresol is methylated in the liquid phase to yield 2,6-xylenol and 2,3,6-trimethylphenol in high selectivity and mild conditions.

8 Claims, No Drawings

LIQUID PHASE METHYLATION OF ORTHO CRESOL

This invention relates to the liquid phase methylation of phenolic compounds. More specifically, this invention relates to the liquid phase methylation of ortho cresol to produce 2,6-xylenol and 2,3,6-trimethylphenol.

2,6-xylenol is useful as a precursor to 2,3,6-trimethylphenol and other useful products. 2,3,6-trimethylphenol is useful as an intermediate in Vitamin E synthesis. 2,6-xylenol also finds uses in polymer and plastics applications such as that described in U.S. Pat. No. 3,446,856.

2,6-xylenol is currently prepared using vapor phase methylation. However, when methylation is carried out in a vapor phase reaction, the useful catalyst life is extremely limited and numerous undesirable by-products are formed such as tetra and pentamethyl phenols. 2,6-xylenol is also produced using a magnesium oxide catalyst as described in U.S. Pat. No. 3,446,856. However, this process also has severe disadvantages. A very low space velocity is used along with reaction conditions of about 450° to 500° C and requires a high methanol: o-cresol mole ratio of about 10:1. A method for obtaining highly useful and versatile 2,6-xylenol while avoiding the disadvantages of the prior art processes would be extremely desirable.

Both vapor and liquid phase methylation of phenolics is well known. An example of such methylation techniques can be found in German Pat. No. 1,817,243. Liquid phase methylation is preferable to vapor phase methylation because less severe reaction conditions can be used. Fewer desirable by-products are also produced. However, in prior art liquid phase methods, catalyst life, while superior to that taught for vapor phase, is still undesirably limited. Excessively long residence times and excessively high pressures have also heretofore been required.

It is therefore an object of the present invention to provide an improved process for the liquid phase methylation of ortho cresol to produce 2,6-xylenol and 2,3,6-trimethylphenol. Other objects will become apparent to those skilled in this art as the description proceeds.

In accordance with the present invention, an improved process for selectively producing 2,6-xylenol and 2,3,6-trimethylphenol in the liquid phase methylation of ortho cresol is provided. The process is an improvement over the heretofore known processes in several regards, giving unexpected and dramatic results. High conversion of the ortho cresol and high selectivity to 2,6-xylenol are obtained while reaction time and pressures are reduced significantly.

Concisely, the improved process of the present invention comprises a. reacting ortho cresol with methanol in liquid phase
b. at a temperature of from about 340° to 380° C
c. at a pressure of from about 400 to 600 pounds per square inch gauge (psig)
d. at a liquid hourly spaced velocity (LHSV) of from about 1 to about 15, while
e. in contact with an alumina catalyst derived from aluminum alkoxide hydrolysis.

In carrying out the process of the present invention, from about 0.2 to about 1.0 mols of methanol or other methylating agent such as isobutylene are used per mole of ortho cresol, but from about 0.4 to about 0.7 mols are preferred. Prior art processes have taught essentially pure ortho cresol in order to carry out the methylation in a liquid phase in a practical manner. However, in the prevent invention, the ortho cresol can have impurities comprising 2,6-xylenol, phenol, and meta and para cresols without affecting the basic process. Phenol will be methylated to ortho cresol. 2,6-xylenol will be methylated primarily to 2,3,6-trimethylphenol, and meta and para cresols will be methylated to 2,4/2,5-xylenol and 2,3/3,5-xylenol. While pure ortho cresol is preferred in the present invention, very acceptable results can be obtained with high percentage of cresylic impurities. Cresylics as used in this specification and claims comprise a mixture of phenolic compounds.

The process of the present invention can be carried out efficiently in a batch reactor or a continuous flow reactor. Of these, the continuous flow reactor is preferred. In the continuous flow reactor, the residence time in the reactor ranges from about 5 to about 15 minutes compared to prior art reaction times in the liquid phase of 20–60 minutes. Most preferred reaction conditions in the present invention are temperatures of from about 350° to 370° C, residence times of from 7 to 12 minutes, pressures of from 425 to 500 pounds per square inch gauge, liquid hourly space velocities of from 3 to about 7, and mol ratios of methanol/ortho cresol of from 0.3 to 0.7.

The method by which the alumina catalyst is made has been discovered to have an effect on the reaction. While the reason is not known, aluminas derived from alumina alkoxide hydrolysis have been discovered to produce superior results when compared to aluminas obtained from other sources. Examples of such desired aluminas are CATAPAL aluminas and DISPAL aluminas sold by Continental Oil Company. These aluminas, which preferentially absorb methanol, appear to show enhanced reactivity when the cresylic acid component of the reactants is in the liquid phase. In contrast, other prior art catalysts such as titanium oxide and magnesium oxide preferentially absorb cresylic acid and show decreased activity in the liquid phase reaction.

Temperature criticality is determined by conversion of the ortho cresol to the desired product. 2,3,6-trimethylphenol, while in a minor proportion, is an extremely useful product and can also be recovered using conventional methods such as fractional distillation and/or recrystallization for extremely pure products. Methylation temperature of from about 300° to about 390° C can be used.

Selectivities to 2,6-xylenol of over 70 percent can be obtained when the conversion of ortho cresol is around 40 percent. Selectivities to 2,3,6-trimethylphenol of over 12 percent can be obtained while maintaining the selectivity to 2,6-xylenol at over 70 percent. Selectivity is defined as the total production of the desired product (also called productivity) divided by the total cresylic acids excepting anisoles and unconverted ortho cresol which can be recycled as a feedstock along with any other cresylic by-products formed. As previously explained, side reactions of other cresylic components will not affect the process of the present invention.

The invention is more concretely described with reference to the example below wherein all parts and percentages are by weight unless otherwise specified. The example is intended to illustrate the invention and does not limit it.

The data disclosed herein were generated using a one-half inch stainless steel reactor containing one-sixteenth inch diameter alumina extrudate. Flow in the reactor could be varied either upward or by gravity. The reactor contained approximately 60 cubic centimeters of catalyst. The catalyst used was CATAPAL SB alumina. The reactor was heated using an electric furnace. Temperature was measured in the center of the reactor by a thermocouple. No cooling was provided. Temperatures given in the example are the maximum temperatures of the reaction stream in the catalyst zone. After leaving the reactor, the product stream was condensed and product distribution was determined using gas-liquid chromatography (GLC). Actual percentages of products were measured using a computerized program which measured the area under GLC curves.

EXAMPLE 1

Ortho cresol was methylated at a temperature ranging from 355° to 370° C under a pressure of 425 pounds per square inch gauge and an LHSV of approximately 5. The results of 4 separate tests are shown in Table 1.

TABLE 1

| LIQUID PHASE METHYLATION OF o-CRESOL | | | | |
|---|---|---|---|---|
| MeOH Mole Ratio | 0.5 | 0.6 | 0.7 | 0.8 |
| LHSV | 5.7 | 5.2 | 5.3 | 5.3 |
| Temperature, ° C | 360 | 360 | 355 | 370 |
| Phenolics, Wt % in Product | 90.59 | 90.56 | 89.68 | 87.56 |
| Product Composition Wt % | | | | |
| Anisole | 0.05 | 0.06 | 0.04 | 0.05 |
| Phenol | 0.37 | 0.33 | 0.00 | 0.43 |
| o-Methylanisole | 2.43 | 2.71 | 1.48 | 1.64 |
| o-Cresol | 62.79 | 57.33 | 56.67 | 52.45 |
| m,p-Cresol | 0.08 | 0.25 | 0.12 | 0.21 |
| 2,6-Dimethylanisole | 0.16 | 0.23 | 0.12 | 0.17 |
| 2,6-Xylenol | 25.89 | 28.87 | 29.68 | 30.25 |
| 2,4/2,5-Xylenol | 1.29 | 1.43 | 1.74 | 2.13 |
| 2,3/3,5-Xylenol | 1.38 | 1.45 | 1.45 | 1.46 |
| 2,4,6-Trimethylphenol | 0.40 | 0.61 | 0.77 | 1.23 |
| 2,3,5/2,4,5-Trimethylphenol | 3.71 | 4.68 | 5.02 | 5.98 |
| 2,3,5/2,4,5-Trimethylphenol | 0.09 | 0.11 | 0.12 | 0.21 |
| 2,3,4/3,4,5-Trimethylphenol | 0.12 | 0.14 | 0.19 | 0.37 |
| 2,3,4,6 | | | | |
| 2,3,5,6-Tetramethylphenol | 0.84 | 1.18 | 1.41 | 2.06 |
| 2,3,4,5-Tetramethylphenol | 0.00 | 0.00 | 0.04 | 0.11 |
| Pentamethylphenol | 0.39 | 0.62 | 0.77 | 1.25 |
| Productivity (% X Conversion) | | | | |
| 2,6-Xylenol | 23.45 | 26.12 | 26.63 | 26.49 |
| 2,3,6-Trimethylphenol | 3.27 | 4.23 | 4.50 | 5.16 |

It can be clearly seen that 2,6-xylenol and 2,3,6-trimethylphenol are produced in acceptable yields under mild conditions and high selectivities. The data shows that by-product formation, particularly undesirable tetramethylphenols and pentamethylphenols is at a minimum. The process provides high conversion and selectivity per pass through the reactor. Under the mild conditions used in the present invention, catalyst life is much improved over the prior art.

It can be seen that the present invention gives high selectivity to the desired products. It will be apparent that the improved process provided herein is much superior to those provided by the prior art. Catalyst life is extended, selectivities are increased, and impure feedstocks can be used while using reaction conditions of reduced pressure, lower temperature, and less methylating agent than those taught to be necessary by the prior art.

While certain embodiments and details have been shown for the purpose of illustrating this invention, it will be apparent to those skilled in this art that various changes and modifications may be made herein without departing from the spirit or the scope of the invention.

I claim:

1. A process for the liquid phase methylation of ortho cresol to produce 2,6-xylenol and 2,3,6-trimethylphenol comprising:
   a. contacting ortho cresol with methanol in liquid phase,
   b. at a temperature of from about 300° to about 390° C,
   c. at a pressure of from about 400 to about 600 psig, while
   d. in contact with an alumina catalyst derived from aluminum alkoxide hydrolysis.

2. A process as described in claim 1 wherein the reaction is carried out in a continuous flow reactor.

3. A process as described in claim 2 wherein the temperature is from about 340° to about 380° C.

4. A process as described in claim 3 wherein 2,6-xylenol is the desired product.

5. A process as described in claim 2 wherein the liquid hourly space velocity is from about 1 to about 15.

6. A process as described in claim 1 wherein the unreacted ortho cresol is recovered and reused as a feedstock.

7. A process as described in claim 1 wherein the mole ratio of methanol/o-cresol is from 0.3 to 0.7.

8. A process as described in claim 7 wherein the liquid hourly space velocity is from about 2 to about 8.

* * * * *